(12) United States Patent
Kimura

(10) Patent No.: US 8,298,557 B2
(45) Date of Patent: Oct. 30, 2012

(54) CLEANSING COSMETIC COMPOSITION

(75) Inventor: Tomohiko Kimura, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/000,349

(22) PCT Filed: Jun. 16, 2009

(86) PCT No.: PCT/JP2009/002720
§ 371 (c)(1),
(2), (4) Date: Feb. 10, 2011

(87) PCT Pub. No.: WO2009/153963
PCT Pub. Date: Dec. 23, 2009

(65) Prior Publication Data
US 2011/0123650 A1    May 26, 2011

(30) Foreign Application Priority Data
Jun. 19, 2008   (JP) .................... 2008-159940

(51) Int. Cl.
*A61Q 1/14*   (2006.01)
(52) U.S. Cl. ........................................ 424/401
(58) Field of Classification Search ........... None
See application file for complete search history.

(56) References Cited

U.S. PATENT DOCUMENTS

| | | | | |
|---|---|---|---|---|
| 2005/0186167 A1* | 8/2005 | Ueda et al. | ............... | 424/70.13 |
| 2005/0287088 A1* | 12/2005 | Guiramand et al. | ............ | 424/59 |

FOREIGN PATENT DOCUMENTS

| JP | 62135406 A | 6/1987 |
|---|---|---|
| JP | 1211513 A | 8/1989 |
| JP | 3161428 A | 7/1991 |
| JP | 9110638 A | 4/1997 |
| JP | 9249520 A | 9/1997 |
| JP | 9249522 A | 9/1997 |
| JP | 2003252726 A | 9/2003 |
| JP | 2004026791 A | 1/2004 |
| JP | 2004217640 A | 8/2004 |
| JP | 2004238376 A | 8/2004 |
| JP | 2005068082 A | 3/2005 |
| JP | 2005104892 A | 4/2005 |
| JP | 2005314358 A | 11/2005 |
| JP | 2006022004 A | 1/2006 |
| JP | 2006232717 A | 9/2006 |
| JP | 2007023025 A | 2/2007 |

OTHER PUBLICATIONS

Japanese Office Search Report for PCT/JP2009/002720 dated Jul. 30, 2009, (JP and English 6 pages).
JP 2008-159940—Written Amendment filed on Oct. 21, 2008 for JP App. 2008-159940 (1 page—JP); English Translation full (1 page); Certificate of Translation (1 page).
JP 2008-159940—Notice of reasons for refusal: Reference No. PJ0226SSD:Dispatch No. 749992:Dispatch: Date Dec. 5, 2008 (4-pages); English Translation full (4 pages); Certificate of Translation (1 page).
JP 2008-159940—Written Amendment: Reference No. PJ0226SSD:JP2008-159940 (Proof): Submission Date: Jan. 27, 2009 (3 pages); English Translation full (3 pages); Certificate of Translation (1 page).
JP 2008-159940—Written Argument: Reference No. PJ0226SSD:JP2008-159940 (Proof): Submission Date: Jan. 27, 2009 (5 pages); English Translation full (6 pages); Certificate of Translation (1 page).
JP 2008-159940—Decision to Grant a Patent (3 pages); English Translation full (3 pages); Certificate of Translation (1 page).
JP Pat. No. B 4274491 (granted patent of JP 2008-159940) (Japanese 11 pages); English Translation full (23 pages); Certificate of Translation (1 page).

* cited by examiner

*Primary Examiner* — Jyothsna Venkat
(74) *Attorney, Agent, or Firm* — Andrew F. Young, Esq.; Lackenbach Siegel, LLP

(57) ABSTRACT

It is intended to provide a cleansing cosmetic composition that quickly removes makeup from the skin, is easily applicable onto the skin without dripping from the hand or running on the face during application, and can freshen the skin because of being washed off thoroughly. The present invention provides a cleansing cosmetic composition comprising (1) 1 to 15% by mass of silicone oil, (2) 1 to 15% by mass of volatile hydrocarbon oil, (3) 5 to 20% by mass of dihydric glycol, (4) 5 to 40% by mass of polyoxyethylene glyceryl fatty acid ester, and (5) 15 to 88% by mass of water, wherein the weight ratio between the silicone oil (1) and the volatile hydrocarbon oil (2) ((1)/(2)) falls within the range of 0.3 to 3 and the composition has a viscosity of 100 to 500 mPas at 25° C.

1 Claim, No Drawings

CLEANSING COSMETIC COMPOSITION

CROSS REFERENCE TO RELATED APPLICATIONS

This application relates to and claims priority from PCT/JP2009/002720 filed Jun. 16, 2009, the entire contents of which are incorporated herein by reference, which in turn claims priority from JP 2008-159940 (now granted) filed Jun. 19, 2008.

FIGURE SELECTED FOR PUBLICATION

No figures

BACKGROUND OF THE INVENTION

1. Field of the Invention

The present invention relates to a cleansing cosmetic composition that has a high cleansing power for makeup, particularly, difficult-to-remove makeup such as mascara, can quickly remove makeup from the skin, is easily applicable onto the skin without dripping, etc., in use, and is washed off thoroughly.

2. Description of the Related Art

For makeup cleansing, easy applicability onto the skin and quick removal of makeup from the skin are demanded. In general, cleansing cosmetic compositions used in makeup cleansing are broadly classified into two: wipe-off and wash-off types. Particularly, wipe-off type has been used in conveniently removing makeup composed mainly of oil, such as mascara or lipstick.

The wipe-off type is a manner in which a tissue or cotton is moistened with a cleansing cosmetic composition, the melting action of which helps makeup come off, and thus, the makeup is wiped off with the tissue or cotton. Since the high melting action of oil contained in the cleansing cosmetic composition influences its makeup cleansing power, the selection of the formulated oil is important. As this type of cleansing cosmetic composition, for example, a nonaqueous cleansing composition has been proposed which is formulated with isoparaffin hydrocarbon, chain dimethylpolysiloxane, and other oils (Patent Document 1).

However, such wipe-off type cleansing cosmetic compositions present the problem of wastes of used tissues or cottons. In addition, compositions consisting of oil cannot be washed off with water, leaving the oil on the skin. Thus, they fail to produce freshness and comfort.

To solve such problems, bases have been developed which comprise oil that is easily rinsed off. They contain 50% or more liquid oil which is formulated with a surfactant therein. Such formulations are provided with water washability such that the surfactant emulsifies the oil during washing off with water. These compositions are generally called cleansing oils. Briefly, the characteristics of the wash-off type are added to those of the wipe-off type.

As specific examples of such cleansing oils, there have been proposed a composition comprising liquid oil, a nonionic surfactant in a liquid or paste state, and 0.1 to 2.0% by weight of water (Patent Document 2), a composition comprising a mixture of 60 to 85% by weight of a liquid oil agent and a nonionic surfactant, and 12% by weight or less of water (Patent Documents 3 and 4), etc. The cleansing oils are characterized in that the oil and the surfactant occupy the most part of the composition, as in the wipe-off type, and water is formulated in a small amount.

However, the cleansing oils, which contain a large amount of oil, are unpleasant due to an oily feel during application and are also unpleasant due to the viscosities of emulsions formed from the oil washed off with water, leaving a slimy feel on the skin. Moreover, the cleansing oils with the composition as described above are in a liquid state having a viscosity as low as 100 mPa□ s or lower, usually 70 mPa□s or lower, and therefore have presented the problem that they are difficult to apply because of dripping when put on the hand for application or running on the face during application.

To solve the oiliness of the cleansing oils, an isotropic one-liquid-phase cleansing composition has also been proposed which strikes a balance between oil components and water-soluble solvents (Patent Document 5). This cleansing composition is allegedly capable of removing both oily and hydric soils.

However, such a cleansing composition cannot overcome the dripping problem seen in cleansing oils, because the composition has a low viscosity, albeit with reduced oiliness. Moreover, this cleansing composition has also presented problems in safety or usability (e.g., sore eyes resulting from the cleansing composition that has entered the eyes), because it comprises ester or ether of a lauryl or tetradecyl group and a hydrophilic substance, lauryl alcohol, and lauric acid.

On the other hand, cleansing gels in a gel state or cleansing creams in a cream state have been developed as easily applicable compositions improved in dripping. The cleansing gels refer to compositions whose viscosity is enhanced with an acrylic thickener, water-soluble polysaccharides, agar, a cellulose thickener, or the like to disperse oil. Based on such an approach, methods have been proposed which are intended to prevent dripping from the hand or face during application and allow a cleansing composition to easily blend into makeup (Patent Documents 6 to 9).

However, when such a polymer thickener is used, it has presented the problem of unpleasantness attributed to a slimy feel left on the skin after rinse with water.

Moreover, the cleansing creams have a viscosity derived from an O/W-type emulsified state, which prevents dripping from the hand or face during application and allows the composition to easily blend into makeup. Therefore, to melt makeup into the oil, the emulsified state must be destroyed to release the oil. Thus, the blending into makeup takes much time, and quick removal of makeup is difficult to achieve. Moreover, they also have presented the problem that dirt in minute areas in pores or sulcus cutis on the skin is difficult to remove due to their high viscosities.

Thus, although various types of cleansing cosmetic compositions have previously been proposed, a cleansing cosmetic composition that is easily applicable onto the skin without dripping, quickly removes makeup from the skin, and is washed off thoroughly has not been obtained so far. Its development has been demanded.

PRIOR ART PUBLICATIONS

Patent Documents

Patent Document 1: JP-A-Hei 1-211513
Patent Document 2: JP-A-Hei 3-161428
Patent Document 3: JP-A-2004-238376
Patent Document 4: JP-A-2004-26791
Patent Document 5: JP-A-2004-217640
Patent Document 6: JP-A-Sho 62-135406
Patent Document 7: JP-A-Hei 9-110638
Patent Document 8: JP-A-Hei 9-249520
Patent Document 9: JP-A-Hei 9-249522

ASPECTS AND SUMMARY OF THE INVENTION

Problem to be Solved by the Invention

The present invention has been achieved in consideration of the problems of the conventional techniques. An object of the present invention is to provide a cleansing cosmetic composition that quickly removes makeup from the skin, is easily applicable onto the skin without dripping from the hand or running on the face during application, and can freshen the skin because of being washed off thoroughly.

Means for Solving the Problem

The present inventors have conducted diligent studies and consequently completed the present invention by finding that a cleansing cosmetic composition that contains silicone oil and volatile hydrocarbon oil at a particular ratio, further contains dihydric glycol, polyoxyethylene glyceryl fatty acid ester, and water, and has a viscosity within a particular range can solve all the problems described above.

Specifically, the present invention provides a cleansing cosmetic composition comprising
(1) 1 to 15% by mass of silicone oil,
(2) 1 to 15% by mass of volatile hydrocarbon oil,
(3) 5 to 20% by mass of dihydric glycol,
(4) 5 to 40% by mass of polyoxyethylene glyceryl fatty acid ester represented by the following formula:

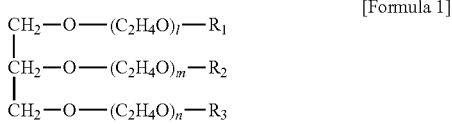

[Formula 1]

wherein at least one of $R_1$, $R_2$, and $R_3$ represents a saturated or unsaturated higher aliphatic hydrocarbon group having 14 to 22 carbon atoms, and the other moieties each represent a hydrogen atom; and l, m, and n each represent a positive integer, and
(5) 15 to 88% by mass of water, wherein, the weight ratio between the silicone oil (1) and the volatile hydrocarbon oil (2) ((1)/(2)) falls within the range of 0.3 to 3 and the cleansing cosmetic composition has a viscosity of 100 to 500 mPa·s at 25° C.

Effects of Invention

A cleansing cosmetic composition according to the present invention is easily applicable onto the skin without dripping from the hand or running on the face in use, and can freshen the skin because of being washed off thoroughly. Moreover, the cleansing cosmetic composition of the present invention has a high cleansing power, is less irritating (e.g., less smarting eyes), and is also excellent in its functions and safety.

The above, and other aspects, features and advantages of the present invention will become apparent from the following description read in conjunction with the accompanying drawings, in which like reference numerals designate the same elements.

BRIEF DESCRIPTION OF THE DRAWINGS

None

DETAILED DESCRIPTION OF THE PREFERRED EMBODIMENTS

Reference will now be made in detail to embodiments of the invention that are illustrated in the discussion herein.

EMBODIMENTS FOR CARRYING OUT THE INVENTION

Silicone oil (component (1) described above) used in a cleansing cosmetic composition according to the present invention may be any of volatile and non-volatile silicone oils and can be selected appropriately from those conventionally used in cosmetics, etc.

Examples of the volatile silicone oil include: chain silicone oils (chain polysiloxanes) such as decamethyltetrasiloxane, hexamethyldisiloxane, and dodecamethylpentasiloxane; and cyclic silicone oils (cyclic polysiloxanes) such as hexamethylcyclotrisiloxane, octamethylcyclotetrasiloxane, decamethylcyclopentasiloxane, and methylpolycyclosiloxane.

Examples of the non-volatile silicone oil include modified silicone oils such as dimethylpolysiloxane, phenylmethylpolysiloxane, methylhydrogenpolysiloxane, polyether-modified silicone, alkyl-modified silicone, higher fatty acid ester-modified silicone, higher alkoxy-modified silicone, phenol-modified silicone, fluorine-modified silicone, and cross-linked organopolysiloxane.

Among these silicone oils, decamethylcyclopentasiloxane and phenylmethylpolysiloxane are particularly preferable from the viewpoint of a makeup cleansing power, though the silicone oil is not limited to them.

In the present invention, one of or two or more of such volatile and/or non-volatile silicone oils may be used.

The amount of the silicone oil formulated in the cleansing cosmetic composition of the present invention is 1 to 15% by mass, preferably 2 to 10% by mass. When the amount of the silicone oil formulated is smaller than 1% by mass, the resulting composition has an insufficient makeup cleansing power. When the silicone oil is formulated in an amount exceeding 15% by mass, the resulting composition is unpleasant due to a strong oily feel during blending into makeup and is not favorable in terms of feeling of residues after washing off.

Volatile hydrocarbon oil (component (2) described above) used in the cleansing cosmetic composition according to the present invention is cyclic or linear hydrocarbon oil appropriately selected from those conventionally used in cosmetics, etc., and may be formulated alone or as a mixture. Non-volatile hydrocarbon oil tends to remain on the skin and does not freshen the skin after rinsing. In addition, it is not excellent in oily texture after towel dry. Thus, it is important for the cleansing cosmetic composition of the present invention to use volatile hydrocarbon oil.

Examples of the volatile hydrocarbon oil that can be used in the present invention can include isoparaffins. Specific examples of the isoparaffins include light isoparaffin, light liquid isoparaffin, heavy liquid isoparaffin, liquid isoparaffin, hydrogenated polyisobutene, isohexadecane, and isododecane. Among them, isododecane and isohexadecane are particularly preferable in terms of a makeup cleansing power.

The amount of the volatile hydrocarbon oil formulated in the cleansing cosmetic composition of the present invention is 1 to 15% by mass, preferably 2 to 10% by mass. When the amount of the volatile hydrocarbon oil formulated is smaller than 1% by mass, the resulting composition has an insufficient makeup cleansing power. When the amount of the volatile hydrocarbon oil formulated exceeds 15% by mass, the resulting composition is unpleasant due to a strong oily feel during blending into makeup and is not favorable in terms of residues after washing off.

General makeup cosmetic compositions, for example, foundation, lipstick, and mascara, often contain silicone oil and hydrocarbon oil. For cleansing off such makeup, it is important that the composition well blends into these oil components. Therefore, the cleansing cosmetic composition of the present invention, which contains both the silicone oil and the hydrocarbon oil (volatile), is particularly effective for cleansing off such makeup.

The cleansing cosmetic composition of the present invention has a weight ratio between the silicone oil and the volatile hydrocarbon oil (silicone oil/volatile hydrocarbon oil) that falls within the range of 0.3 to 3, more preferably 0.5 to 2. As a result, the cleansing cosmetic composition exerts an excellent makeup cleansing power. When this ratio is smaller than 0.3 or larger than 3, the resulting composition tends to have a reduced cleansing power and offer no fresh feel after rinse.

Dihydric glycol (component (3) described above) used in the cleansing cosmetic composition according to the present invention is one or two or more selected from, but not limited to, for example, 1,3-butylene glycol, 1,4-butylene glycol, 2,3-butylene glycol, 2,3-dimethyl-2,3-butylene glycol, dipropylene glycol, and ethylene glycol.

The dihydric glycol according to the present invention may play a role in adjusting the viscosity of the composition, mildly cleansing the skin, and stabilizing the composition.

The amount of the dihydric glycol formulated in the cleansing cosmetic composition of the present invention is 5 to 20% by mass, preferably 5 to 15% by mass. When the amount of the dihydric glycol formulated is smaller than 5% by mass, the resulting composition has a reduced viscosity and low moisturizes the cleansed skin. When the amount of the dihydric glycol formulated exceeds 20% by mass, the resulting composition tends to have poor stability.

Polyoxyethylene glyceryl fatty acid ester (component (4) described above) used in the cleansing cosmetic composition according to the present invention is selected from those represented by the following formula:

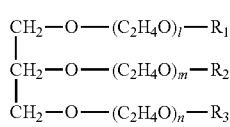
[Formula 2]

wherein at least one of $R_1$, $R_2$, and $R_3$ represents a saturated or unsaturated higher aliphatic hydrocarbon group having 14 to 22 carbon atoms, and the other moieties each represent a hydrogen atom; and l, m, and n each represent a positive integer.

In the present invention, among the polyoxyethylene glyceryl fatty acid esters represented by the formula above, monoester forms are particularly preferable, and those having an average degree of ethylene oxide polymerization of 6 to 20, more preferably 7 to 10, in one molecule are preferable. The formulation of such polyoxyethylene glyceryl fatty acid ester selected further improves the makeup cleansing power and the fresh feel after washing off. Specific examples thereof include polyoxyethylene (8) glyceryl monoisostearate, polyoxyethylene (10) glyceryl monoisostearate, and polyoxyethylene (20) glyceryl monoisostearate.

The amount of the polyoxyethylene glyceryl fatty acid ester formulated in the cleansing cosmetic composition of the present invention is 5 to 40% by mass, preferably 20 to 35% by mass. When the amount of the polyoxyethylene glyceryl fatty acid ester formulated is smaller than 5% by mass, the resulting composition poorly rinses during washing off. When the amount of the polyoxyethylene glyceryl fatty acid ester formulated exceeds 40% by mass, the resulting composition may be irritating to the skin or eyes.

The cleansing cosmetic composition of the present invention comprises, in addition to the components (1) to (4), 15 to 88% by mass, preferably 30 to 70% by mass of water (component (5) described above). When the amount of water formulated is smaller than 15%, the resulting composition hardly offers a fresh feel in use or a moisture feel during application. When the amount of water formulated exceeds 88% by mass, the resulting composition has a reduced makeup cleansing power.

The cleansing cosmetic composition of the present invention has a viscosity that is adjusted, as a whole, to 100 to 500 mPa·s at 25° C. When the viscosity is lower than 100 mPa·s, the resulting composition has problems in use such as dripping from the hand or running on the face during application. When the viscosity exceeds 500 mPa·s, the resulting composition has a reduced makeup cleansing power because the base hardly enters minute projections and depressions on the skin surface. In addition, the resulting composition is poorly spreadable during application.

The cleansing cosmetic composition according to the present invention may be formulated with, in addition to the essential components (1) to (5), a surfactant without impairing the effect of the present invention. The surfactant used in the present invention is not particularly limited by types and can be selected appropriately from anionic, cationic, amphoteric, and nonionic surfactants.

Furthermore, the cleansing cosmetic composition according to the present invention can be formulated with, in addition to the surfactant, components usually used in cosmetic compositions or pharmaceuticals, without impairing the effect of the present invention.

Examples of the components that can be formulated therein include moisturizers, powder components, liquid oil and fat, solid oil and fat, waxes, hydrocarbon oil, higher fatty acid, higher alcohol, synthetic ester oil, natural water-soluble polymers, semi-synthetic water-soluble polymers, synthetic water-soluble polymers, thickeners, UV absorbers, sequestering agents, lower alcohol, polyhydric alcohol, monosaccharide, oligosaccharide, polysaccharide, amino acids, organic amine, polymer emulsions, pH adjusters, antioxidants, antioxidative aids, antiseptics, antiphlogistics, skin-lightening agents, various extracts, excipients, blood circulation enhancing agents, antiseborrheic agents, and anti-inflammatory agents.

EXAMPLES

Hereinafter, the present invention will be described more specifically with reference to Examples. However, the present invention is not limited to them. In the present specification, amounts formulated mean % by mass, unless otherwise specified.

Each cleansing cosmetic composition with composition described in Examples 1 to 5 and Comparative Examples 1 to 11 (Tables 1 to 3) below was prepared and evaluated for its makeup cleansing power, fresh feel after rinse (after cleansing), appearance stability, viscosity, and pain in eyes. The evaluation results are also shown in Tables 1 to 3.

Each item was evaluated according to the following evaluation criteria:

(A) Makeup Cleansing Power

Actual usability test was conducted by ten expert panelists on the makeup cleansing power of the composition of each Example or Comparative Example. Three kinds of commercially available mascaras with difficult-to-remove indication were used as makeup to be cleansed off. Evaluation criteria are as follows, and these scores were averaged:
- 5: sufficiently removed
- 4: almost removed
- 3: ordinary
- 2: slightly unremoved
- 1: unremoved (B) Fresh Feel after Rinse Makeup was cleansed off with the cleansing cosmetic composition of each Example or Comparative Example, and actual usability test was conducted by ten expert panelists on a fresh feel after rinse with water. Evaluation criteria are as follows, and these scores were averaged:
- 5: offering a fresh feel
- 4: slightly offering a fresh feel
- 3: ordinary
- 2: offering few fresh feels
- 1: offering no fresh feel (C) Appearance Stability Each composition was placed in a cubic container of 2 cm square and visually observed from the side for its transparency at 25° C. When the composition was a single uniform layer through which the other side of the container was seen, it was determined as being transparent (stable):
- A: transparent
- X: opaque (including a state of two or more layers)

(D) Viscosity

The viscosity of the cleansing cosmetic composition of each Example or Comparative Example was measured at 25° C. using a Brookfield viscometer, and the obtained values of viscosity were classified as follows:
Measurement values of 100 to 500 mPa·s: A: good
Measurement values lower than 100 mPa·s or exceeding 500 mPa·s: X: poor (E) Pain in Eyes The cleansing cosmetic composition of each Example or Comparative Example was actually used by 20 persons. When even one person complained of pain in the eye, it was indicated as "X". When no one complained of pain in the eye, it was indicated as "A".

As shown in Table 1 above, the cleansing cosmetic compositions of Comparative Examples 1 and 2, which were free from silicone oil and volatile hydrocarbon oil, were inferior in makeup cleansing power. As a result, usability in which the makeup was removed thoroughly could not be obtained.

On the other hand, the cleansing cosmetic composition of Comparative Example 3, which was free from dihydric glycol, was inferior in makeup cleansing power, had poor appearance stability, and also low moisturized the skin. Moreover, the composition of Comparative Example 4, which was free from polyoxyethylene glyceryl monoisostearate, failed to remove the makeup, while the composition of Comparative Example 5 formulated with PEG12 laurate was improper due to pain in eyes.

TABLE 2

|  | Ex. 2 | Ex. 3 | Com. Ex. 6 | Com. Ex. 7 |
|---|---|---|---|---|
| Ion-exchange water | balance | balance | balance | balance |
| Dipropylene glycol | 10 | 10 | 10 | 10 |
| Decamethylcyclopentasiloxane | 3 | 1 | 1 | 0.5 |
| Isododecane | 1 | 3 | 0.5 | 1 |
| PEG8 glyceryl monoisostearate | 30 | 30 | 30 | 30 |
| Volatile hydrocarbon oil/silicone oil | 3 | 0.33 | 2 | 0.5 |
| Makeup cleansing power | 4.2 | 4.2 | 3.4 | 3.6 |
| Fresh feel after rinse | 4.2 | 4.2 | 3.4 | 3.4 |
| Appearance stability (transparency) | A | A | A | A |
| Viscosity | A | A | A | A |

As shown in Table 2 above, the cleansing cosmetic compositions of Comparative Examples 6 and 7 containing silicone oil or volatile hydrocarbon oil formulated in an amount smaller than 1% were inferior in makeup cleansing power. Thus, usability in which the makeup was removed thoroughly could not be obtained.

TABLE 1

|  | Ex. 1 | Com. Ex. 1 | Com. Ex. 2 | Com. Ex. 3 | Com. Ex. 4 | Com. Ex. 5 |
|---|---|---|---|---|---|---|
| Ion-exchange water | balance | balance | balance | balance | balance | balance |
| Dipropylene glycol | 10 | 10 | 10 | 0 | 10 | 10 |
| Decamethylcyclopentasiloxane | 10 | 0 | 10 | 10 | 10 | 10 |
| Isododecane | 10 | 10 | 0 | 10 | 10 | 10 |
| PEG8 glyceryl monoisostearate | 30 | 30 | 30 | 30 | 0 | 0 |
| PEG12 monolaurate |  |  |  |  |  | 30 |
| Volatile hydrocarbon oil/silicone oil | 1 | 0 | ∞ | 1 | 1 | 1 |
| Makeup cleansing power | 4.8 | 2.6 | 2.4 | 4.2 | 2.5 | 4.2 |
| Fresh feel after rinse | 4.8 | 3.4 | 3.6 | 3.8 | 2.6 | 3.8 |
| Appearance stability (transparency) | A | A | A | X | X | A |
| Viscosity | A | A | A | X | X | X |
| Pain in eye | A | A | A | A | A | X |

TABLE 3

| | Ex. 4 | Ex. 5 | Com. Ex. 8 | Com. Ex. 9 | Com. Ex. 10 | Com. Ex. 11 |
|---|---|---|---|---|---|---|
| Ion-exchange water | balance | balance | balance | balance | balance | balance |
| Dipropylene glycol | 10 | 10 | 10 | 10 | 10 | 10 |
| Decamethylcyclopentasiloxane | | 10 | 10 | 2 | 10 | 10 |
| Phenylmethylpolysiloxane | 10 | | | | | |
| Isododecane | 10 | | | 2 | 10 | 10 | 10 |
| Isohexadecane | | 10 | | | | |
| PEG8 glyceryl monoisostearate | 30 | 30 | 30 | 30 | 3 | 50 |
| Volatile hydrocarbon oil/silicone oil | 1 | 1 | 5 | 0.2 | 1 | 1 |
| Makeup cleansing power | 4.8 | 4.8 | 3.8 | 3.8 | 3 | 4.4 |
| Fresh feel after rinse | 4.6 | 4.6 | 3.8 | 3.8 | 2.8 | 4.6 |
| Appearance stability (transparency) | A | A | A | A | X | A |
| Viscosity | A | A | A | A | A | X |
| Pain in eye | A | A | A | A | A | X |

As shown in Table 3 above, the cleansing cosmetic compositions of Comparative Examples 8 and 9 having a weight ratio between silicone oil and volatile hydrocarbon oil larger than 3 or smaller than 0.3 were inferior in makeup cleansing power. Thus, usability in which the makeup was removed thoroughly could not be obtained.

Moreover, the composition of Comparative Example 10 containing polyoxyethylene glyceryl monoisostearate formulated in an amount smaller than 5% by mass was inferior in makeup cleansing power, while the composition of Comparative Example 11 containing larger than 40% by mass of polyoxyethylene glyceryl monoisostearate was confirmed to have too high viscosity and sometimes produce pain in eyes.

Example 6

A makeup cleansing cosmetic composition with the following composition was prepared:

| Component | Amount formulate (% by mass) |
|---|---|
| Water | balance |
| Isododecane | 5% |
| Isohexadecane | 2% |
| Liquid paraffin | 0.5% |
| Decamethylcyclopentasiloxane | 5% |
| Phenylmethylpolysiloxane | 3% |
| Glycerin | 0.5% |
| Dipropylene glycol | 5% |
| 1,3-butylene glycol | 7% |
| PEG8 glyceryl isostearate | 30% |
| Alcohol | 3% |
| Citric acid | 0.1% |
| Sodium citrate | 0.5% |
| Moisturizing amino acid | 0.1% |
| Green tea extract | 0.1% |
| Peppermint extract | 0.1% |
| Iris florentina root extract | 0.1% |
| Chamomilla extract | 0.1% |
| Ascorbic acid glucoside | 0.1% |
| L-serine | 0.05% |
| Chelating agent | q.s. |
| Antioxidant | q.s. |
| Perfume | q.s. |

(Production Method)

These components above were mixed into ion-exchange water at room temperature to obtain a cleansing cosmetic composition. The cleansing cosmetic composition of Example 6 was excellent in makeup cleansing power, offered a fresh texture after rinse, and had excellent stability and excellent usability without dripping from the hand.

Unless otherwise defined, all terms (including technical and scientific terms) used herein have the same meaning as commonly understood by one of ordinary skill in the art to which this invention belongs. It will be further understand that terms, such as those defined in commonly used dictionaries, should be interpreted as having a meaning that is consistent with their meaning in the context of the relevant art and will not be interpreted in an idealized or overly formal sense unless expressly so defined herein.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. A cleansing cosmetic composition comprising:
(1) 1 to 15% by mass of silicone oil,
(2) 1 to 10% by mass of volatile hydrocarbon oil,
(3) 10 to 20% by mass of dihydric glycol,
(4) 5 to 40% by mass of polyoxyethylene glyceryl monoisostearate having an average degree of ethylene oxide polymerization in a number ranging from 6 to 20 in one molecule; and
(5) 15 to 88% by mass of water,
wherein, the weight ratio between the silicone oil (1) and the volatile hydrocarbon oil (2) ((1)/(2)) falls within the range of 0.3 to 3 and the cleansing cosmetic composition has a viscosity of 100 to 500 mPa·s at 25° C.
wherein the silicone oil (1) is selected from the group consisting of cyclic polysiloxane and phenylmethylpolysiloxane; and
wherein the volatile hydrocarbon oil (2) is a mixture of isododecane and isohexadecane.

* * * * *